US012595475B2

(12) United States Patent
Farinas et al.

(10) Patent No.: US 12,595,475 B2
(45) Date of Patent: Apr. 7, 2026

(54) METHODS AND SYSTEMS FOR EXTRACTING NUCLEIC ACIDS FROM A BIOLOGICAL SAMPLE

(71) Applicant: Kryptos Biotechnologies, Inc., Hayward, CA (US)

(72) Inventors: Javier Farinas, Los Altos, CA (US); Jun Ho Son, Albany, CA (US)

(73) Assignee: Kryptos Biotechnologies, Inc., Hayward, CA (US)

( * ) Notice: Subject to any disclaimer, the term of this patent is extended or adjusted under 35 U.S.C. 154(b) by 961 days.

(21) Appl. No.: 17/748,824

(22) Filed: May 19, 2022

(65) Prior Publication Data

US 2022/0372465 A1     Nov. 24, 2022

Related U.S. Application Data

(60) Provisional application No. 63/191,083, filed on May 20, 2021.

(51) Int. Cl.
*C12N 15/10*        (2006.01)

(52) U.S. Cl.
CPC ................................ *C12N 15/1013* (2013.01)

(58) Field of Classification Search
CPC ......... C12N 15/1013; B01L 2200/0631; B01L 2200/0673; B01L 2400/043; B01L 3/502761
See application file for complete search history.

(56) References Cited

U.S. PATENT DOCUMENTS

2002/0022261 A1*   2/2002   Anderson ............. B01L 3/5027
                                          435/287.9
2014/0127773 A1*   5/2014   Brown ............. G01N 33/54313
                                           435/174
(Continued)

FOREIGN PATENT DOCUMENTS

EP           2921231 A1     9/2015
EP           3337897 B1     3/2020
(Continued)

OTHER PUBLICATIONS

PCT/US2022/030338, "Invitation to Pay Additional Fees And, Where Applicable, Protest Fee", Aug. 11, 2022, 3 pages.
(Continued)

*Primary Examiner* — Jennifer Wecker
*Assistant Examiner* — Britney N. Washington
(74) *Attorney, Agent, or Firm* — Kilpatrick Townsend & Stockton LLP

(57) ABSTRACT

A method for extracting nucleic acids includes mixing a biological sample with a solid-phase substrate to produce a sample fluid. The nucleic acids in the sample fluid bind to the solid-phase substrate. The method also includes flowing the sample fluid in a fluid conduit to a trapping site. The trapping site may include a chamber. The method may further include applying a magnetic field to trap the solid-phase substrate of the sample fluid flowing through the fluid conduit at the trapping site. The method further includes flowing a wash buffer through the fluid conduit to remove impurities from the solid-phase substrate. The method further includes flowing an immiscible fluid through the fluid conduit to remove residual sample fluid and/or wash buffer. The method further includes flowing an elution buffer through the fluid conduit to elute nucleic acids from the solid-phase substrate.

11 Claims, 9 Drawing Sheets

(56) References Cited

U.S. PATENT DOCUMENTS

| | | | | | |
|---|---|---|---|---|---|
| 2014/0335527 | A1* | 11/2014 | Goel | ................. | B01L 3/502753 |
| | | | | | 435/6.12 |
| 2016/0102341 | A1* | 4/2016 | Curran | .............. | B01L 3/502784 |
| | | | | | 506/40 |
| 2018/0095067 | A1* | 4/2018 | Huff | ................. | G01N 33/48721 |

FOREIGN PATENT DOCUMENTS

| | | | |
|---|---|---|---|
| WO | 2008110019 | A1 | 9/2008 |
| WO | 2012096780 | A1 | 7/2012 |
| WO | 20141 44209 | A1 | 9/2014 |
| WO | 2014207577 | A2 | 12/2014 |

OTHER PUBLICATIONS

Application No. PCT/US2022/030338, International Preliminary Report on Patentability, Mailed on Nov. 30, 2023, 9 pages.
Chen et al., Magnetic Particles for Integrated Nucleic Acid Purification, Amplification and Detection Without Pipetting, Trends in Analytical Chemistry, vol. 127, May 6, 2020, 13 pages.
European Application No. 22805618.0, Extended European Search Report mailed on Mar. 6, 2025, 9 pages.
Application No. PCT/US2022/030338, International Search Report and Written Opinion, Mailed on Oct. 5, 2022, 18 pages.

* cited by examiner

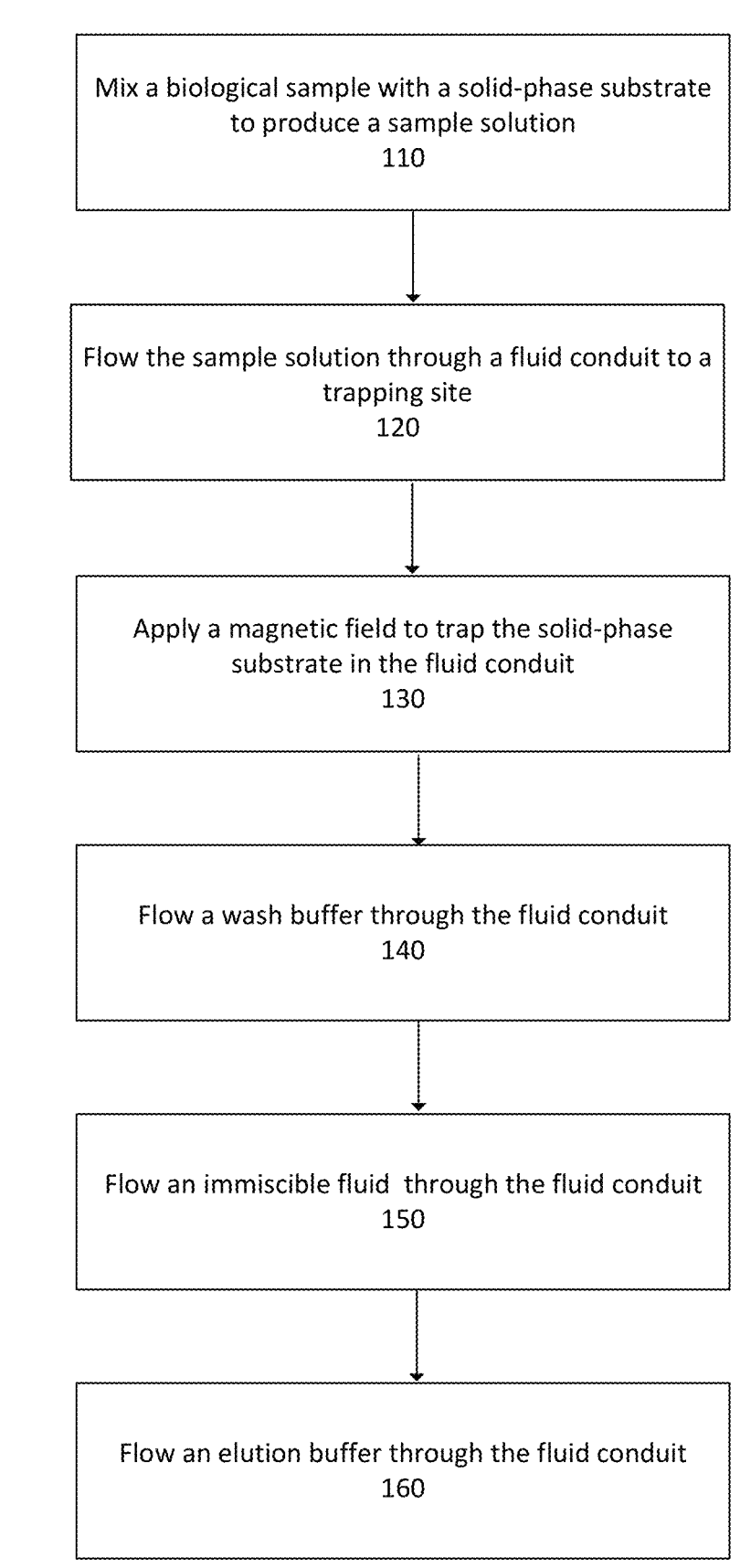

100

Mix a biological sample with a solid-phase substrate
to produce a sample solution
110

Flow the sample solution through a fluid conduit to a
trapping site
120

Apply a magnetic field to trap the solid-phase
substrate in the fluid conduit
130

Flow a wash buffer through the fluid conduit
140

Flow an immiscible fluid  through the fluid conduit
150

Flow an elution buffer through the fluid conduit
160

*FIG. 1*

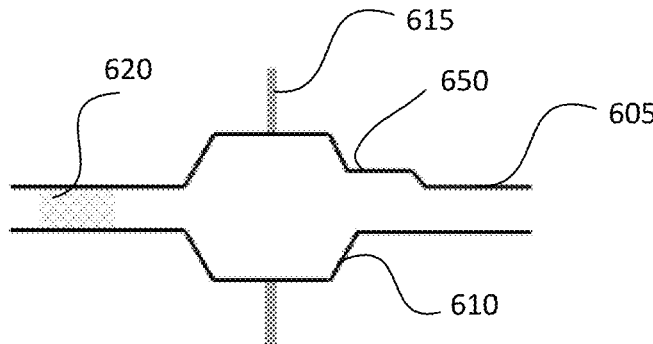
*FIG. 6A*
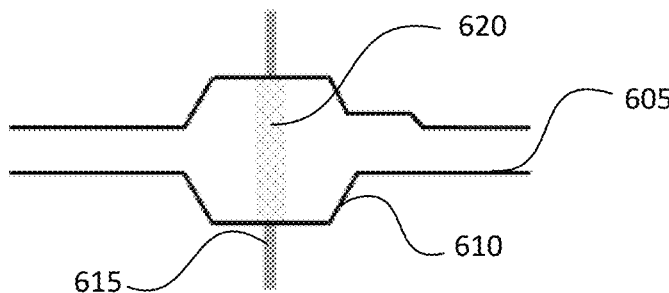
*FIG. 6B*
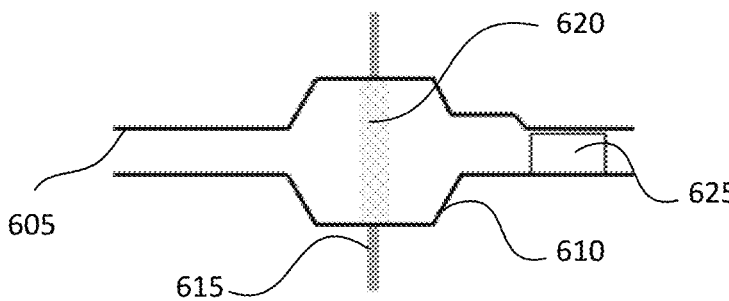
*FIG. 6C*
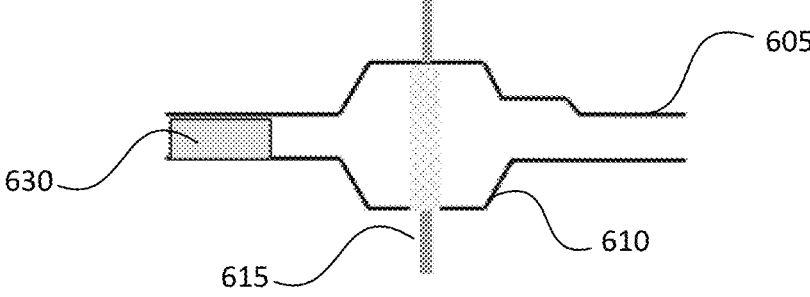
*FIG. 6D*

METHODS AND SYSTEMS FOR EXTRACTING NUCLEIC ACIDS FROM A BIOLOGICAL SAMPLE

CROSS-REFERENCE TO RELATED APPLICATION

This application claims the benefit of and priority to U.S. Provisional Application No. 63/191,083, filed May 20, 2021, the disclosure of which is hereby incorporated by reference in its entirety.

BACKGROUND OF THE INVENTION

Methods of isolating nucleic acids from complex starting materials like whole blood, blood serum, urine, respiratory tract secretions, comprise lysis of biological material in the presence of protein inactivating conditions (e.g., protein degrading enzymes), followed by separation of nucleic acids from contaminants by methods including solvent precipitation, solid phase extraction, and dialysis of the nucleic acids. The isolation of nucleic acid is an important step in many biochemical and diagnostic procedures. For example, the separation of nucleic acids from the complex mixtures in which they are often found is needed before other studies and procedures are conducted, e.g., detection, cloning, sequencing, amplification, hybridization, cDNA synthesis, etc. However, the presence of large amounts of cellular or other contaminating material, e.g., proteins, carbohydrates, or salts, in such complex mixtures often impedes many of the reactions and techniques used in molecular biology. Thus, improved methods for isolating and extracting nucleic acids from complex mixtures are needed for diagnosis of microbial infections, forensic science, tissue and blood typing, detection of genetic variations, etc.

SUMMARY OF THE INVENTION

This disclosure relates to methods and systems suitable for extracting nucleic acids from a biological sample.

In some embodiments, the present disclosure provides a method for extracting nucleic acids. The method includes mixing a biological sample with a solid-phase substrate to produce a sample fluid. The nucleic acids in the sample fluid bind to the solid-phase substrate. The method also includes flowing the sample fluid in a fluid conduit to a trapping site. The trapping site may include a chamber. The method further includes applying a magnetic field to trap the solid-phase substrate of the sample fluid flowing through the fluid conduit at the trapping site. The method further includes flowing a wash buffer through the fluid conduit to remove impurities from the solid-phase substrate. The method further includes flowing an immiscible fluid through the fluid conduit to remove residual sample fluid and/or wash buffer. The method further includes flowing an elution buffer through the fluid conduit to elute nucleic acids from the solid-phase substrate.

In some embodiments, the present disclosure provides a system for extracting nucleic acids. The system includes a fluid conduit; a chamber disposed along a length of the fluid conduit, the chamber having a cross-sectional area larger than an average cross-sectional area of the fluid conduit; a magnetic field source disposed along discrete regions of the chamber; and a controller coupled to the magnetic field source and configured to vary (e.g., oscillate) the magnetic field source.

Numerous benefits are achieved by way of the present invention over conventional techniques. For example, embodiments of the present invention speed up the overall extraction process, result in higher yields of nucleic acids, and minimize interferences with downstream assays. In some embodiments, flowing an immiscible fluid in a fluid conduit following one or more washing steps entirely removes residual washing fluids, including residual contaminants, so that the drying of the fluid conduit is not necessary and it is possible to elute nucleic acids directly after this step. In some embodiments, the fluid conduit for extracting and isolating nucleic acids includes a chamber for trapping the solid-phase substrate in the fluid conduit to increase contact between fluids and the solid-phase substrate, thereby removing residual components (e.g., supernatant) from the solid-phase substrate. These and other embodiments of the disclosure, along with many of its advantages and features, are described in more detail in conjunction with the text below and corresponding figures.

BRIEF DESCRIPTION OF THE DRAWINGS

The disclosure will be readily understood by the following detailed description in conjunction with the accompanying drawings, wherein like reference numerals designate like structural elements, and in which:

FIG. 1 shows a flow diagram of a method of extracting nucleic acids according to embodiments of the present invention.

FIGS. 6A-H are simplified schematic cross-sectional view diagrams illustrating a fluid conduit extraction system according to an embodiment of the present invention.

DETAILED DESCRIPTION OF SPECIFIC EMBODIMENTS

Figures 2A, 2B, 2C, 2D, 2E:
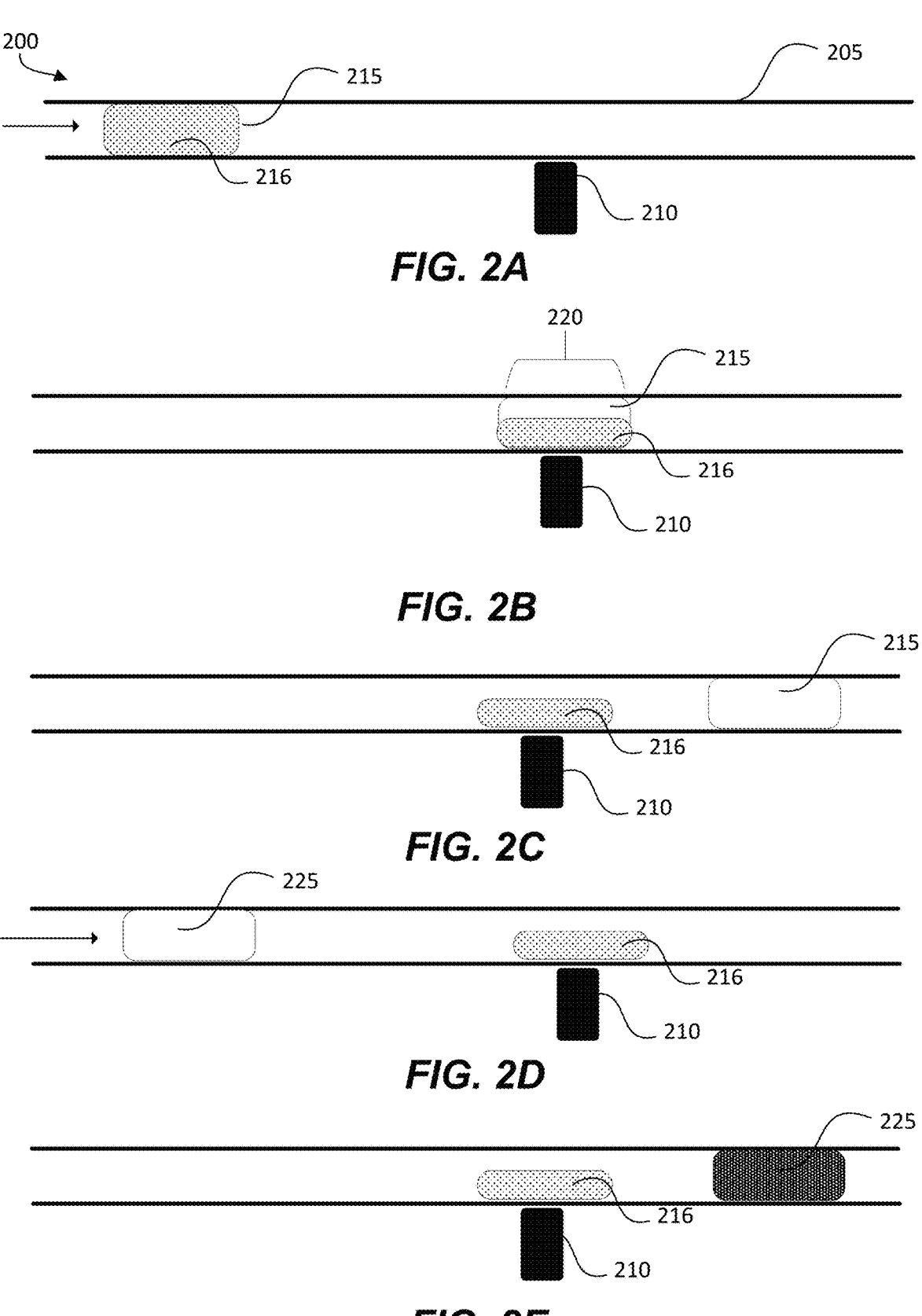
FIGS. 2A-2N are simplified schematic cross-sectional view diagrams illustrating a fluid conduit extraction system according to an embodiment of the present invention.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting; such that other embodiments may be used, and changes may be made without departing from the spirit and scope of the described embodiments.

Conventional methods of isolating nucleic acids generally require an initial nucleic acid isolation step, to separate the nucleic acid from materials that may interfere in the detection, hybridization, and/or amplification techniques that are used. A range of methods are known for the isolation of nucleic acids, but these rely on a complex series of extraction and washing steps and are time consuming and laborious to perform. For example, methods for isolating nucleic acids from complex starting materials involve lysis of the biological material, possibly in the presence of protein degrading enzymes, followed by several extractions with organic solvents, ethanol precipitation, centrifugations, and dialysis of the nucleic acids. Not only are such methods cumbersome and time consuming to perform, but the relatively large number of steps required increases the risk of degradation, sample loss, or cross-contamination of samples where several samples are simultaneously processed.

Solid phase extraction is one method of isolating and extracting nucleic acids from a biological sample. During solid phase extraction, nucleic acids in a biological sample bind to a solid-phase substrate. In some embodiments, the solid-phase substrate can be plurality of beads coated with silica or other materials. The solid-phase substrate (e.g., beads) are then washed with alcohol-based or other solutions to remove the supernatant and loosely bound impurities from the nucleic acids bound to the solid-phase substrate. For example, the solid-phase substrate is washed with a low pH wash buffer or an alcohol-based wash buffer to remove any interfering substances before assaying the extracted nucleic acids. As used herein, a "low pH wash buffer" may be a wash buffer having pH less than 7 (e.g., less than 6, less than 5, less than 4, less than 3, or less than 2). To remove residual wash buffer components which may interfere with downstream processes, the surface of the solid-phase substrate is dried (e.g., using air) after one or more washing steps. After washing and drying the solid-phase substrate, the nucleic acids are eluted from the solid-phase substrate with a low ionic strength water-based buffer.

Since many of the reagents used in the solid phase extraction process interfere with downstream assays, it is typically necessary to remove any interfering substances before assaying the extracted nucleic acids. For example, guanidinium salts used in the lysis buffers are typically removed so as to not interfere with downstream assays. Conventionally, several alcohol-based washes are conducted to remove residual salts from the system. In addition, the alcohol-based wash buffers (e.g., ethanol, propanol, etc.), which are often used in the washing steps, are also removed in order to have high extraction yields and prevent interference with downstream assays. In order to remove the alcohol-based wash buffers, the process typically requires drying the solid-phase substrate, for example, by flowing air over the solid-phase substrate, heating the solid-phase substrate, or applying a negative pressure to the solid-phase substrate. This introduces limitations on the procedure and is often hard to achieve in cartridges, particularly for cartridges that automate sample preparation. For example, high temperatures are sometimes used to evaporate the ethanol; however, high temperatures can degrade nucleic acids, particularly RNA. When air drying the solid-phase substrates, substantial time is required to remove or reduce the alcohol-based wash buffers to acceptable levels (typically less than 1 wt. % in the elute).

Embodiments of the present invention provide methods and systems for eluting nucleic acids from a solid-phase substrate that utilize an immiscible fluid to remove residual reagents or impurities (e.g., alcohol-based wash buffers) from the solid-phase substrate. In some embodiments, the method provides a means to elute nucleic acids bound to surfaces of a solid-phase substrate as part of nucleic acid purification process that uses an immiscible fluid instead of air drying to get rid of residual reagents. In particular embodiments, an immiscible fluid (e.g., mineral oil) is utilized that does not extract nucleic acids from the solid-phase substrate, but preferentially removes wash buffers (e.g., alcohols), salts, or other interfering substances. The use of such immiscible fluids speeds the overall extraction process, results in higher yields, and minimizes interferences with downstream assays.

Additionally, specific advantages have been found when using the aforementioned immiscible fluid with a specifically designed fluid conduit for isolating and extracting nucleic acids. Conventional fluid conduits utilize a conduit with a uniform cross-sectional area in which the solid-phase substrate may be trapped in some region of the fluid conduit. In the fluid conduit, a series of lysis, wash, and elution buffers can be passed through the conduit for isolating and extracting the nucleic acids. However, these methods do not provide adequate contact for the lysis, wash, and elution buffers with the solid-phase substrate. Therefore, a plurality of washes are required to achieve the desired isolation and extraction of the nucleic acids. This leads to longer times for the overall extraction process, lower yields of nucleic acids, increased damage to the nucleic acids, and causes more interference with downstream assays.

In some embodiments, the present disclosure describes a system for extracting and isolating nucleic acids. In some embodiments, the system comprises a fluid conduit including a chamber for trapping the solid-phase substrate in the fluid conduit at a trapping site. In some embodiments, the chamber has a larger cross-sectional area than the fluid conduit for receiving and retaining the solid-phase substrate. For example, the solid-phase substrate can be a plurality of paramagnetic beads comprising a silica coating for adhering a biological sample to the solid-phase substrate. The paramagnetic beads can be trapped in the chamber and a magnetic field can be applied to the chamber to retain the paramagnetic beads in the chamber. The magnetic field or magnetic field gradient can be varied in intensity or orientation while maintaining sufficient force to keep the paramagnetic beads trapped while allowing for better mixing with the sample, wash buffer, immiscible fluid, or elution buffer. A wash buffer can be passed through the fluid conduit. As the wash buffer flows through the chamber containing the paramagnetic beads, the magnetic field can be directed in a plurality of directions (e.g., along the X-axis, Y-axis, or Z-axis) with respect to the chamber to facilitate mixing of the wash buffer with the paramagnetic beads. In this way, there is increased contact between the wash buffer and the solid-phase substrate, thereby removing more residual components (e.g., supernatant) from the solid-phase substrate than would be achieved absent this increased contact. An immiscible fluid can also be passed through the fluid conduit. The magnetic field around the chamber can be selectively controlled (e.g., by changing its position, intensity, orientation or gradient) to improve contact of the working fluid with the solid-phase substrate to preferentially remove the alcohols, salts, or other interfering substances. In some embodiments, other means of trapping the solid-phase substrate are contemplated, for example, trapping beads by a weir in the conduit.

In some embodiments, the method for solid phase extraction of nucleic acids includes mixing a biological sample with a lysis buffer to produce a first fluid. In some aspects, the lysis buffer comprises guanidinium. In some embodiments, the method includes mixing the first fluid with a binding buffer (e.g., an alcohol-based binding buffer optionally comprising a solid-phase substrate) to produce a second fluid. The second fluid is in contact with a solid-phase substrate (e.g., paramagnetic beads) to bind the nucleic acids to the solid-phase substrate. The solid-phase substrate is subsequently washed with fluids such as a low pH wash buffer or an alcohol-based wash buffer to remove any interfering substances (e.g., salts, alcohols, etc.). The method includes introducing an immiscible fluid to remove the wash buffer and any other lysed substances from the solid phase substrate prior to elution.

These and other embodiments are discussed below with reference to the figures, however, those skilled in the art will readily appreciate that the detailed description given herein with respect to these figures is for explanatory purposes only and should not be construed as limiting.

FIG. 1 provides a flow diagram of a method 100 of extracting nucleic acids according to embodiments of the present disclosure. The method 100 includes mixing a biological sample with a solid-phase substrate to produce a sample fluid (110). As known to one of ordinary skill in the art, there are numerous ways to bind nucleic acids in the sample fluid to the solid-phase substrate. For example, a buffer (e.g., lysis buffer) can be mixed with the biological sample to lyse biological structures such as cells, viruses, organelles or other nucleic acid containing structures in the biological sample to release nucleic acids and supernatant from the structures. The nucleic acids released from the cells can bind to the solid-phase substrate. The supernatant may comprise cell wall debris, proteins, and other components within the cell. For example, the supernatant can be components within the biological samples that are not nucleic acids.

In some embodiments, the sample fluid comprises nucleic acids bound to a solid-phase substrate. For example, the solid-phase substrate may comprise a plurality of beads. In this example, the sample fluid comprises nucleic acids from the biological sample bound to the surface of the beads. In some embodiments, other components from the lysed cells in the biological sample may be bound to the beads. In some embodiments, the beads may be magnetic beads or paramagnetic beads. In some embodiments, the beads may be comprised of silica, polymer, or ceramic with a magnetic or paramagnetic core. In some embodiments, the beads can be functionalized (for example with a silica or silica-like coating, with capture oligonucleotides or with charged polymers) to promote binding of nucleic acids, specific types of nucleic acids (e.g., DNA, RNA, or different nucleic acid size ranges) or specific nucleic acid sequences.

The method 100 includes flowing a sample fluid through a fluid conduit to a trapping site (120). For example, the method includes flowing a sample fluid comprising the nucleic acids bound to the solid-phase substrate through the fluid conduit to a trapping site. The trapping site may comprise a chamber within the fluid conduit. In the embodiment shown in FIG. 4, the chamber within the fluid conduit can have a larger cross-sectional area than the fluid conduit.

The method 100 includes applying a magnetic field to trap the solid-phase substrate in the fluid conduit (130). For example, when the trapping site comprises a chamber, the solid-phase substrate in the sample fluid can be trapped in the chamber by applying a magnetic field (e.g., localized magnetic field) to the chamber volume. In particular, the sample fluid flows through the fluid conduit, passing the magnetic field applied to the chamber, whereupon the solid-phase substrate is trapped within the magnetic field, while the other components of the sample fluid continue to flow along the fluid conduit, removing all the unbound molecules (e.g., supernatant) from the sample fluid. In some embodiments, the chamber comprises a shallow region (e.g., a weir). In some embodiments, the solid-phase substrate in the sample fluid is trapped in a shallow region of the chamber.

The method 100 includes flowing a wash buffer through the fluid conduit (140). In some embodiments, one or more wash buffers are passed through the fluid conduit. The wash buffer flows through the fluid conduit passing the localized magnetic field, where the solid-phase substrate is trapped within the magnetic field. The wash buffer extracts loosely bound molecules and residual reagents from the surface of the solid-phase substrate. In some embodiments, the wash buffer comprises an alcohol. In some embodiments, the wash buffer comprises methanol, ethanol, propanol, butanol, or combinations thereof. The wash buffer removes contaminants (e.g., supernatant, unbound cells, etc.) or residual reagents from the solid-phase substrate or the vicinity of the solid-phase substrate. This wash step may be repeated one or more times to remove all contaminants present on the surface of the solid-phase substrate.

The method 100 includes flowing an immiscible fluid through the fluid conduit (150). In some embodiments, the immiscible fluid is a water-immiscible fluid, e.g., mineral oil. The immiscible fluid can remove any residual wash buffer from the surface of the solid-phase substrate. For example, after the wash buffer has passed through the fluid conduit, an immiscible fluid is flowed through the fluid conduit. The immiscible fluid flows within the fluid conduit and passes the localized magnetic field, where the solid phase substrate, for example, implemented in the form of paramagnetic beads, is trapped within the magnetic field. The flow of immiscible fluid removes the wash buffer (e.g., ethanol) from the solid-phase substrate. In some embodiments, the immiscible fluid flows through the fluid conduit and removes alcohols, salts (e.g., from the lysis buffer), or other interfering substances left behind after the wash buffer has passed as described in relation to step 130. Therefore, the immiscible fluid removes any remaining contaminants from the solid-phase substrate. This step may be repeated one or more times to remove all wash buffer present on the surface of the solid-phase substrate.

The method 100 includes flowing an elution buffer through the fluid conduit (160). The elution buffer flows within the fluid conduit and passes the localized magnetic field, where the solid phase substrate is trapped within the magnetic field. The elution buffer elutes (e.g., releases) the nucleic acids from the surface of the solid phase substrate. In some embodiments, the elution buffer may comprise water. In some embodiments, the elution buffer comprises a low pH buffer. The eluted nucleic acids are picked up by the elution buffer and continue to flow along the fluid conduit for further biological processing and analysis. In some embodiments, the following fluids are passed through the fluid conduit: sample fluid, washing buffer, immiscible fluid, and elution buffer. In some embodiments, the following fluids or subsets of the following fluids are passed through the fluid conduit: sample fluid, air gap, washing buffer, air gap, immiscible fluid, air gap, and elution buffer. In some embodiments, the following fluids or subsets of the following fluids are passed through the fluid conduit: sample fluid, air gap, washing buffer, air gap, immiscible fluid, air gap, and elution buffer. In some embodiments, the following fluid mixtures, which can include solids, are passed through the fluid conduit: solid phase substrate, biological sample, lysing buffer, washing buffer, immiscible fluid, and elution buffer.

In some embodiments, the immiscible fluid passes through the fluid conduit prior to the elution buffer to prevent trace elements of wash buffer (e.g., alcohol) along the fluid conduit and/or the solid phase substrate from mixing with the elution buffer. The immiscible fluid can remove, for example, entirely remove, residual washing fluids from the fluid conduit and/or the solid phase substrate, including residual contaminants remaining in the fluid conduit, so that the drying of the fluid conduit or solid phase substrate is not necessary. Therefore, it is possible to elute nucleic acids directly after flowing the immiscible fluid through the fluid conduit.

Therefore, in some embodiments, the present method does not utilize a drying step following the passing of the washing fluid. This drying step, which is utilized in conventional methods, is time consuming and troublesome because additional processing steps (e.g., heating, vacuum, centrifugation) are utilized.

It should be appreciated that the specific steps illustrated in FIG. 1 provide a particular method of extracting nucleic acids according to an embodiment of the present invention. Other sequences of steps may also be performed according to alternative embodiments. For example, alternative embodiments of the present invention may perform the steps outlined above in a different order. Moreover, the individual steps illustrated in FIG. 1 may include multiple sub-steps that may be performed in various sequences as appropriate to the individual step. Furthermore, additional steps may be added or removed depending on the particular applications. One of ordinary skill in the art would recognize many variations, modifications, and alternatives.

Figures 2F, 2G, 2H, 2I, 2J:
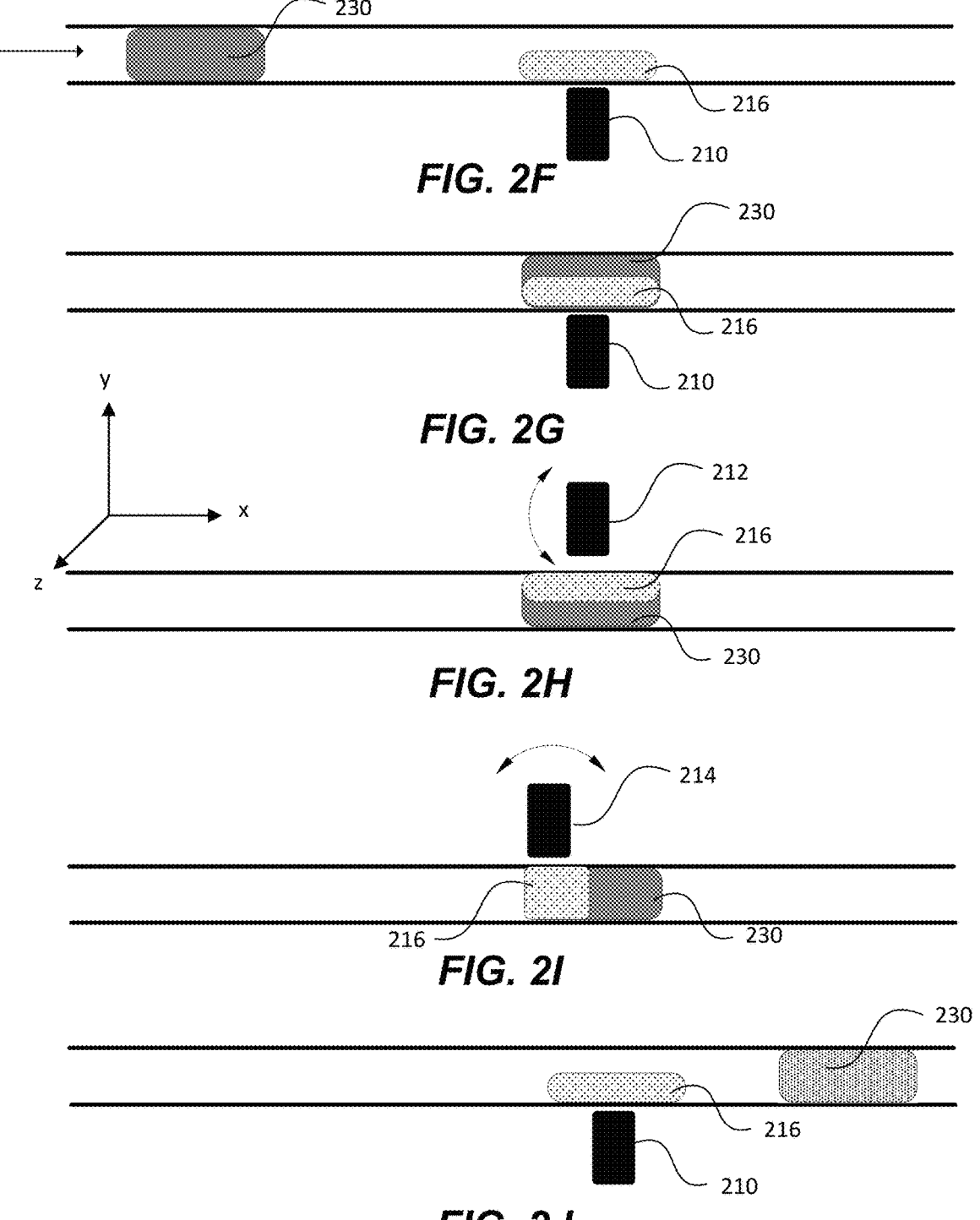
Figures 2K, 2L, 2M, 2N:
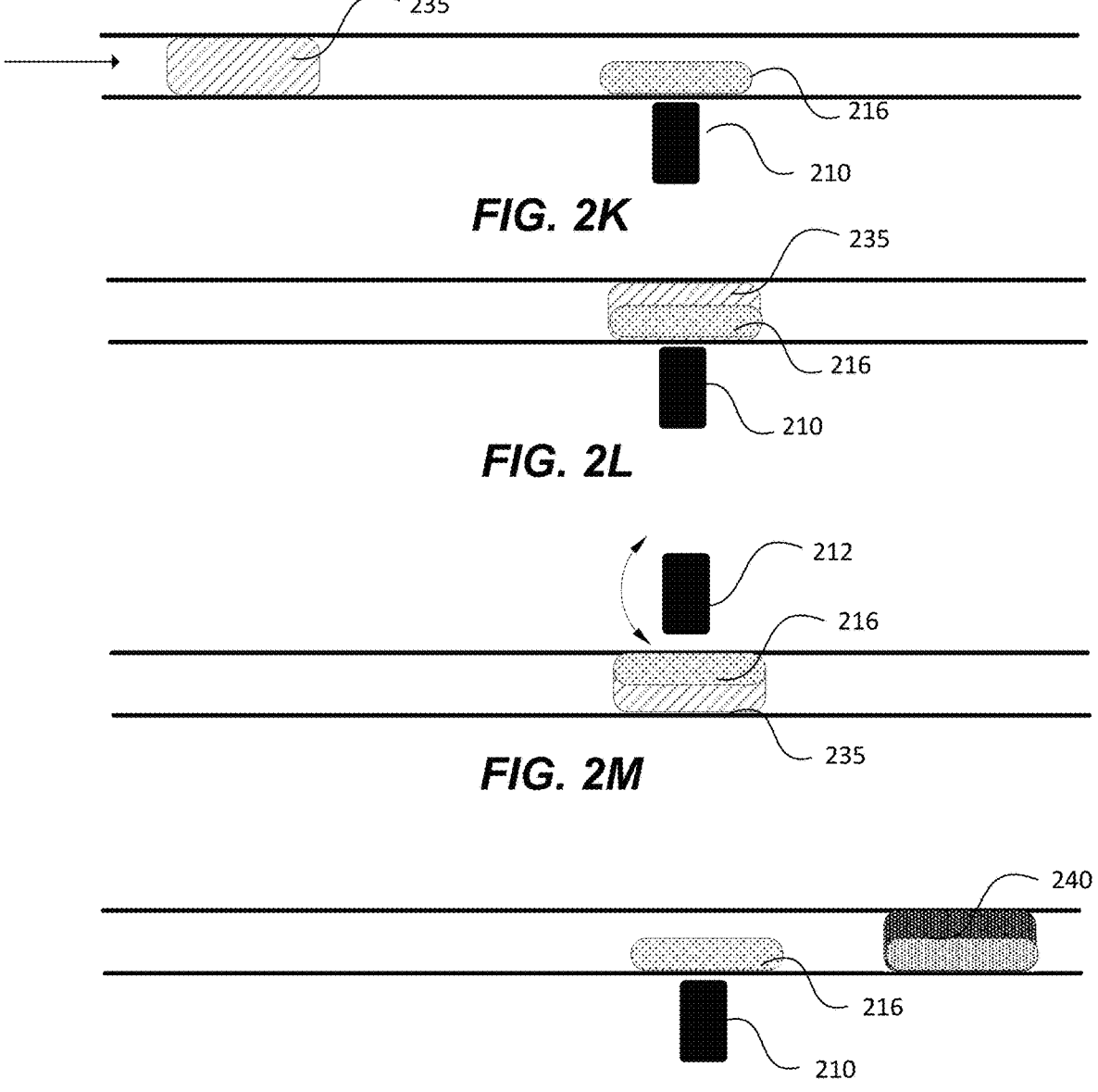

FIGS. 2A-2N are simplified schematic cross-sectional view diagrams illustrating a fluid conduit extraction system according to an embodiment of the present invention. In some embodiments, the system 200 for extracting nucleic acids comprises a fluid conduit 205. For example, the fluid conduit 205 can be a microfluidic channel. The fluid conduit 205 may include a conveying means for supplying the fluids described herein through the fluid conduit. For example, the conveying means may be a pump (not shown) for applying a pressure to the fluid conduit 205 to move the fluid through the fluid conduit 205. The pump may be attached to the fluid conduit for providing a plurality of fluids through the fluid conduit. In some embodiments, the fluid passed through the fluid conduit 205 is passed in the form of a slug. For example, a slug can be a volume of fluid that encompasses the entire cross-section of the fluid conduit. In some embodiments, the fluid conduit 205 may comprise a tube with an airtight seal such that there is a vacuum in the tube. A pump can apply a pressure to move the slug of fluid through the fluid conduit 205.

FIG. 2A shows a slug of sample fluid 215 flowing within a fluid conduit 205. In some embodiments, the slug of sample fluid 215 is drawn through the fluid conduit 205 at various time points and/or speeds. The sample fluid 215 comprises target molecules (e.g., nucleic acids) from a biological sample (e.g., whole blood) adhered to a solid-phase substrate 216 (e.g., paramagnetic beads). In some embodiments, the biological sample can be mixed with a solid-phase substrate prior to being supplied to the fluid conduit 205. In some embodiments, the biological sample may be mixed with one or more buffer solutions and a solid-phase substrate to form the sample fluid 215. For example, the buffer solutions may comprise a lysis buffer and/or a binding buffer. The lysis buffer can lyse cells/organelles in the biological sample and their contents, including nucleic acids, are released into solution. The binding buffer can promote binding of the nucleic acids to the solid-phase substrate 216. In some embodiments, the biological sample is lysed using any method (e.g., by heating, with ultrasound or a suitable lysis fluid). The target molecules from the lysed biological sample can bind to the solid-phase substrate 216. The binding may occur in the sample fluid prior to flowing the sample fluid, or at other points in the process or in another liquid medium.

In some embodiments, the solid-phase substrate 216 can be any suitable substrate that attracts and adheres target molecules from a biological sample. For example, the solid-phase substrate 216 can be one or more of paramagnetic beads, magnetic beads, glass beads, glass fibers, glass membranes, among others. In some embodiments, the solid-phase substrate 216 comprises a plurality of paramagnetic beads optionally including a coating (e.g., silica or capture oligonucleotides). The solid-phase substrate 216 may be used in systems similar to that outlined here to assist in assembling nucleic acid structures. The solid-phase substrate 216 provides large surface to volume ratios useful in exposing relevant bound chemistry. In some embodiments, the solid-phase substrate 216 can be used to isolate and enrich target cells from a biological sample.

Figures 4A, 4B:
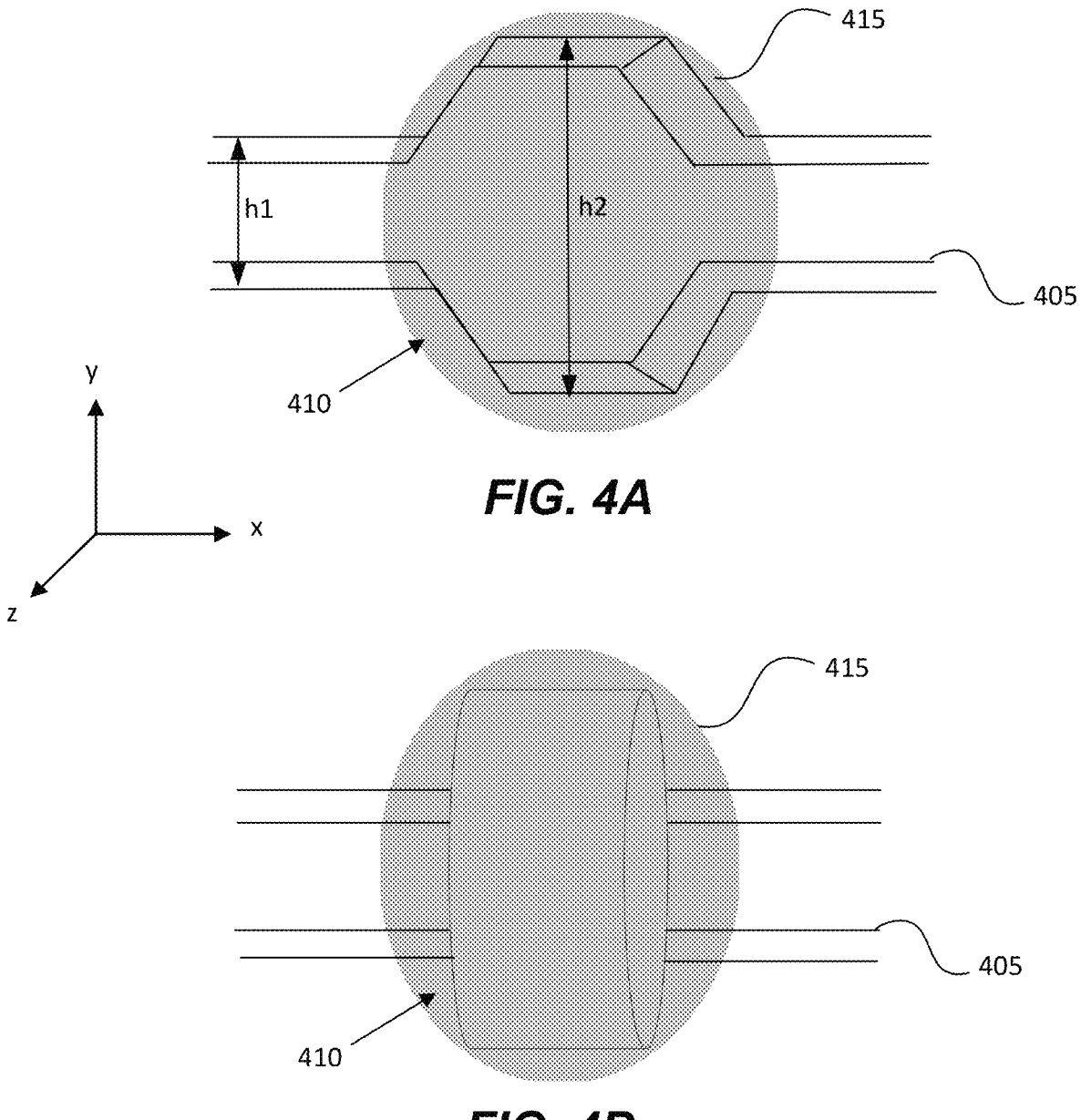
FIGS. 4A and 4B are perspective views of a fluid conduit according to embodiments of the present invention.

FIG. 2B shows the solid-phase substrate 216 trapped within a trapping site 220 of the fluid conduit. In some embodiments, a magnetic field source 210 is adjacent the exterior of the trapping site 220 of the fluid conduit 205. For example, the magnetic field source 210 may be located in a predetermined region for trapping or immobilizing the solid-phase substrate 216 in the sample fluid. As shown in FIGS. 4A and 4B, the fluid conduit may comprise a chamber, which forms the trapping site. The chamber may be located at a predetermined location in the fluid conduit 205 and is configured to trap the solid-phase substrate by applying a magnetic field from a magnetic field source 210. In some embodiments, the fluid conduit 205 comprises a chamber having a larger cross-sectional area than an average cross-sectional area of the fluid conduit. For example, FIGS. 4A and 4B show a chamber 410 that may have an enlarged height, width, and/or length compared to the rest of the fluid conduit. In some embodiments, the chamber may be cylindrical, hexagonal, cuboid, or spherical. The solid-phase substrate 216 can be immobilized within the chamber of the fluid conduit 205.

FIG. 2C shows the supernatant separated from the sample fluid 215. The target biological molecules bound to the solid-phase substrate 216 in the sample fluid 215 are trapped in the fluid conduit 205 using a magnetic field source 210. The unbound portion of the sample fluid 215 continues through the fluid conduit 205. The unbound portion of the sample fluid 215 including the supernatant is then discarded. For example, in embodiments using paramagnetic beads, the slug of sample fluid 215 continues to flow within the fluid conduit 205 while the paramagnetic beads with bound target biological molecules remain trapped in the fluid conduit 205 by the magnetic field source 210.

FIG. 2D shows a slug of wash buffer 225 introduced into the fluid conduit 205. The wash buffer 225 flows through the fluid conduit 205. The wash buffer 225 flows over and through the trapped solid-phase substrate 216 in the fluid conduit 205. In some embodiments, the wash buffer 225 comprises an alcohol. For example, the wash buffer 225 can include ethanol, propanol, or other alcohols, or combinations thereof. One or more slugs of wash buffer 225 can be introduced into the fluid conduit 205. In some embodiments, slugs of fluid can be followed by slugs of air (e.g., air gaps between slugs of fluid). As shown in FIG. 2E, the slug of wash buffer 225 flows within the fluid conduit 205, passing the localized magnetic field, where the solid-phase substrate is trapped within the magnetic field, while the other components of the slug of wash buffer 225 continue to flow along the fluid conduit. The slug of wash buffer 225 removes the loosely bound molecules and residual reagents from the surface of the solid-phase substrate. In other words, the slug of wash buffer 225 cleans contaminants from the solid-phase substrate.

FIG. 2F shows a slug of immiscible fluid 230 introduced into the fluid conduit 205. The slug of immiscible fluid 230 flows through the fluid conduit 205 and passes over and/or through the solid-phase substrate 216. The slug of immiscible fluid 230 may comprise mineral oil, silicone oil, hexadecane, paraffin oil, fluorinerts, fluorinated oils, and mixtures thereof. As shown in FIG. 2G, the slug of immiscible fluid 230 passes through the trapping site including the solid-phase substrate 216 that is trapped by the magnetic field produced by the magnetic field source 210. The immiscible fluid can remove any residual wash buffer from the fluid conduit 205 and the surface of the solid-phase substrate 216.

FIGS. 2I1 and 2I show a magnetic field source 212 positioned at a second location with respect to the fluid conduit 205. In some embodiments, the magnetic field source 210 can be reoriented as shown in FIGS. 2H and 2I. The magnetic field source 212 can produce a magnetic field that can vary (e.g., oscillate) in a plurality of directions around the fluid conduit 205 to move the solid-phase substrate 216 with respect to the fluid conduit 205. For example, magnets can be disposed along discrete regions of the fluid conduit 205 and a controller coupled to the magnetic field source is configured to vary the strength, gradient, and/or orientation of the magnetic field source. In some embodiments, the magnetic field source 212 trapping the solid-phase substrate 216 can be adjusted in one or more directions to promote mixing of one or more fluids (e.g., wash buffer or immiscible fluid) with the solid-phase substrate 216. As shown in FIG. 2I1, the magnetic field source 212 can be translated along the Y-axis (e.g., up and down) to move the solid-phase substrate 216 in the fluid conduit 205. As shown in FIG. 2I, the magnetic field 214 can be translated along the X-axis (e.g., left and right) to move the solid-phase substrate 216 in the fluid conduit 205. The magnetic field 214 can be translated along the Z-axis (e.g., forward and back) to move the solid-phase substrate 216 in the fluid conduit 205. In some embodiments, the controller moves (e.g., oscillates) the magnetic field source in a horizontal or vertical direction (e.g., XYZ direction) with respect to the chamber. FIG. 2J shows the immiscible fluid 230, including any residual wash buffer or contaminants, passing out of the fluid conduit. The magnetic field sources 210 and 212 (or other magnetic field sources) can be present at the same time.

FIG. 2K shows a slug of elution buffer 235 introduced into the fluid conduit 205. The elution buffer 235 flows over and through the solid-phase substrate 216 (FIG. 2L). The slug of elution buffer 235 releases the target biological molecules (e.g., nucleic acids) bound to the solid-phase substrate 216. The released target biological molecules from the solid-phase substrate 216 can be taken up or absorbed by the slug of elution buffer 235. FIG. 2M shows a time-varying magnetic field source 210 located at a position along the fluid conduit 205 to promote contact between the elution buffer and the solid-phase substrate 216. FIG. 2N shows the elution buffer 235 including the eluted target biological molecules leaving the fluid conduit 205 for further processing and/or analysis.

FIGS. 3A-3E are simplified schematic cross-sectional view diagrams illustrating a fluid conduit extraction system according to an embodiment of the present invention. In some embodiments, the system for extracting nucleic acids comprises a fluid conduit 305. For example, the fluid conduit

305 can be a microfluidic channel. The fluid conduit 305 includes a chamber 310 for retaining a solid-phase substrate within a predetermined region of the fluid conduit. The chamber 310 may be located at a predetermined site in the fluid conduit 305.

Figures 3A, 3B, 3C, 3D, 3E:
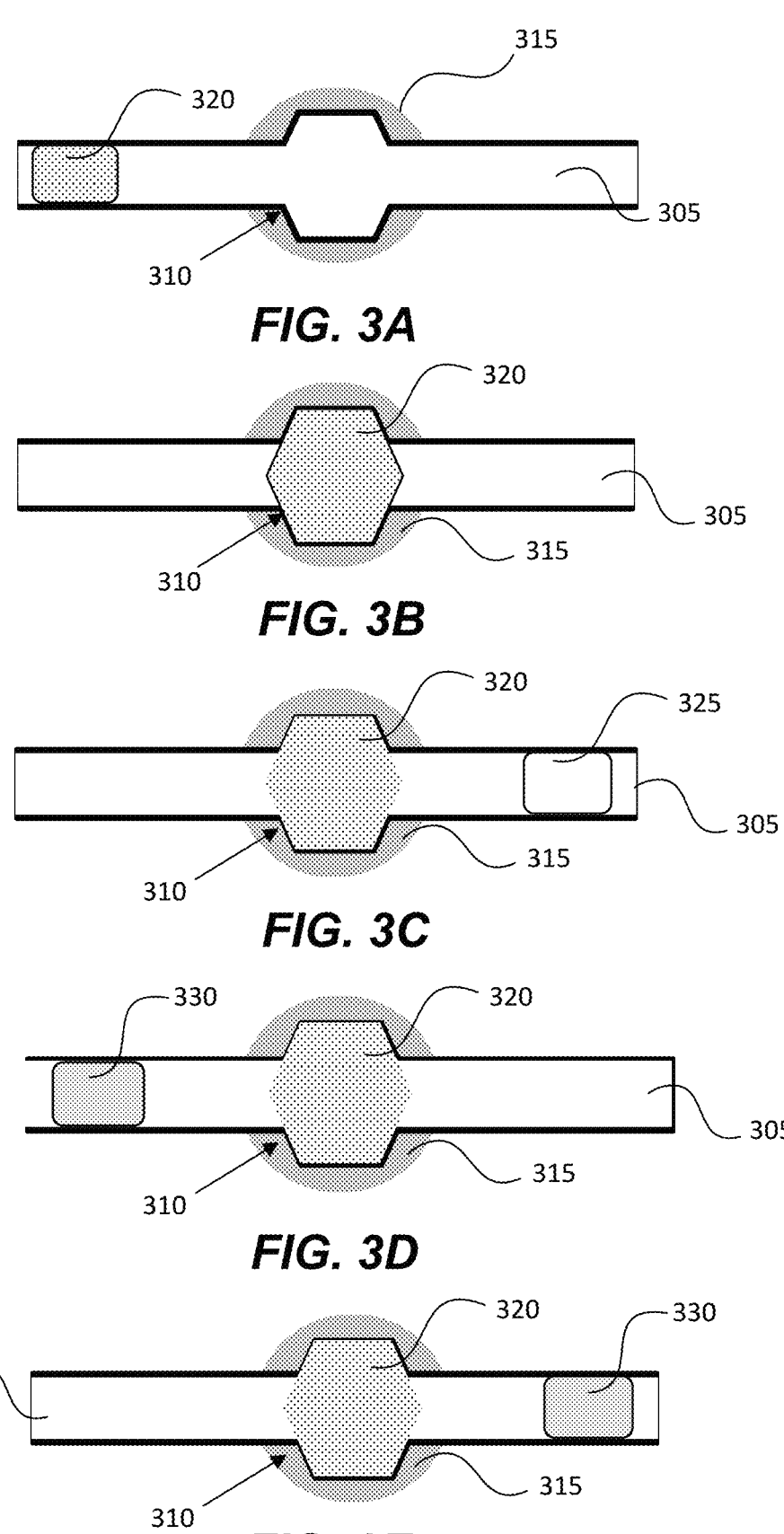
FIGS. 3A-3E are simplified schematic cross-sectional view diagrams illustrating a fluid conduit extraction system according to an embodiment of the present invention.

FIG. 3A shows a slug of sample fluid 320 as it begins to flow through the fluid conduit 305. In some embodiments, the slug of sample fluid 320 comprises target biological molecules bound to a solid-phase substrate. The slug of sample fluid 320 passes through the fluid conduit 305 at a rate of speed. For example, a pump (not shown) can apply variable pressure to regulate the speed of the fluids through the fluid conduit 305. FIG. 3B shows the solid-phase substrate in the sample fluid 320 trapped within chamber 310, which can also be referred to as a trapping site. In some embodiments, one or more magnets are disposed around predetermined regions of the chamber 310. The one or more magnets can be selectively controlled to change or move the magnetic field source 315 to different locations with respect to the chamber 310. When the slug of sample fluid 320 passes through the fluid conduit 305, the magnetic field source 315 can be applied to trap the solid-phase substrate in the slug of sample fluid 320 at the trapping site. In this way, the solid-phase substrate in the sample fluid 320 is trapped in the chamber 310.

FIG. 3C shows the supernatant 325 separated from the sample fluid 320. The target biological molecules bound to the solid-phase substrate in the sample fluid 320 are trapped in the chamber 310 of the fluid conduit 305 using a magnetic field source 315, which can be supplemented by physical structures as illustrated in FIG. 4. The supernatant 325 (e.g., the unbound portion of the sample fluid) continues through the fluid conduit 305. FIG. 3D shows a slug of immiscible fluid 330 introduced into the fluid conduit 305 and FIG. 3E shows the slug of immiscible fluid 330 exiting the fluid conduit 305. In some embodiments, the slug of immiscible fluid 330 flows through the fluid conduit after one or more wash buffers flow through the fluid conduit 305. In some embodiments, one or more slugs of immiscible fluid 330 flow through the fluid conduit, alternating with the one or more slugs of wash buffer, with the last slug being an immiscible fluid to remove any residual wash buffer. In some embodiments, the immiscible fluid comprises mineral oil, silicone oil, hexadecane, paraffin oil, fluorinert, or mixtures thereof. The slug of immiscible fluid 330 flows through the fluid conduit 305 and passes over and through the solid-phase substrate trapped by the magnetic field in the chamber 310 of the fluid conduit 305. In some embodiments, after a wash buffer (e.g., ethanol slug) has passed through the fluid conduit 305, the slug of immiscible fluid 330 is introduced into the fluid conduit 305. The slug of immiscible fluid 330 removes trace elements of wash buffer from the fluid conduit and/or the surface of the solid-phase substrate. Subsequently, a slug of elution buffer is introduced into the fluid conduit 305 to release the target biological molecules from the solid-phase substrate into the elution buffer.

Flowing the immiscible fluid through the fluid conduit, after the washing step and before the elution step, results in the unexpected advantage of reducing or eliminating the process of drying the fluid conduit and/or solid-phase substrate to remove residual washing fluid, which is typically necessary using conventional methods. By eliminating the need for drying the fluid conduit and/or solid-phase substrate result in the unexpected advantage of significantly shortening the duration of the nucleic acid isolation and extraction.

FIGS. 4A and 4B are perspective views of a fluid conduit according to embodiments of the present invention. In some embodiments, the system for extracting nucleic acids comprises a fluid conduit 405. For example, the fluid conduit 405 can be a microfluidic channel. The fluid conduit 405 includes a chamber 410. The chamber 410 can have a depth measured along the Y-axis direction of the fluid conduit 405 for retaining a solid-phase substrate within a trapping site of the fluid conduit 405. A magnetic field source 415 can be present in a region surrounding a portion or all of the chamber 410. In some embodiments, the magnetic field intensity, orientation, gradient strength and gradient orientation can be varied as a function of time while still maintaining sufficient force on the solid-phase substrate to keep the solid-phase substrate trapped in the fluid conduit 405. In some embodiments, the magnetic field produced by the magnetic field source 415 can be moved in one or more predetermined directions around the circumference of the chamber 410 to promote mixing of fluid (e.g., wash buffer, immiscible fluid, or elution buffer) with a solid-phase substrate trapped therein.

In some embodiments, the chamber 410 comprises a larger cross-sectional area than the fluid conduit 405 to trap the solid-phase substrate therein. For example, the fluid conduit 305 comprises a chamber 410 having a larger cross-sectional area than an average cross-sectional area of the fluid conduit 405. In one example, the chamber 410 of the fluid conduit 405 may have an enlarged height measured along the Y-axis of the fluid conduit 405, an enlarged width measured along the Z-axis of the fluid conduit 405, and/or an enlarged length measured along the X-axis of the fluid conduit 405, compared to the rest of the fluid conduit 405. For example, FIG. 4A shows that along the Y-axis of the fluid conduit 405, the height (h1) of the fluid conduit 405 is less than the height (h2) of the chamber 410. Similarly, the width of the fluid conduit 405 may be less than the width of the chamber 410 when measured along the Z-axis of the fluid conduit. In some embodiments, a shape of the chamber 410 may be cylindrical, hexagonal, cuboid, or spherical. The cross-sectional area of the chamber 410 can be at least 5% greater than the average cross-sectional of the area of the fluid conduit, e.g., at least 10% greater, at least 15% greater, at least 20% greater, at least 25% greater, at least 30% greater, at least 40% greater, or at least 50% greater.

In some embodiments, a magnetic field source 415 surrounds a portion of the chamber 410 or the entire chamber 410. For example, the magnetic field source 415 may be located at any location along the length or width of the chamber 410 for trapping or immobilizing the solid-phase substrate. In some embodiments, magnets can be disposed along discrete regions of the chamber 410. A controller can be coupled to the one or more magnets. The controller can be configured to move or oscillate the magnetic field source 415 produced by the one or more magnets. The magnetic field source 415 can be moved in any direction to promote mixing of fluid (e.g., wash buffer or immiscible fluid) with the solid-phase substrate. For example, the magnetic field source 415 can be translated along the Y-axis (e.g., up and down) to move the solid-phase substrate in the chamber 410 of the fluid conduit 405. In another example, the magnetic field source 415 can be translated along the X-axis (e.g., left and right) to move the solid-phase substrate in the chamber 410 of the fluid conduit 405. The movement of the magnetic field source 415 to different areas of the chamber 410 while a fluid (e.g., wash buffer or immiscible fluid) passes the chamber 410 promotes mixing and contact with the solid-phase substrate.

An exemplary method of isolating and extracting nucleic acids is provided. The exemplary method utilizes a mineral oil as a final wash before elution when conducting solid-phase extraction with magnetic silica beads.

A 250 µl of a sample containing SARS-CoV2 RNA at 100 copies/ml, carrier RNA, and total human RNA1 (1 ng/µl) in a viral transport medium was provided. The sample was mixed with 500 µl of 6M Gu-SCN (lysis buffer) and 500 µl of 100% ethanol containing Cytiva Sera-Sil 700 nm paramagnetic beads. After a 1 minute incubation, the beads were magnetically separated from the supernatant in a microfluidic channel. The beads were then washed twice with 500 µl of a low ionic strength 80% ethanol wash buffer. The beads were then washed with 250 µl of PCR-grade mineral oil. The nucleic acids were eluted with 16 µl of TE buffer and assayed by rt-qPCR. Extractions were performed also in tubes. It was found that, compared to air drying the beads after the final wash, the oil wash reduced the time needed for nucleic acid extraction by more than 5 minutes. Additionally, the eluates had higher output RNA concentrations: an average of 970 copies/ml for the oil versus 360 copies/ml for the air drying.

Figure 5:
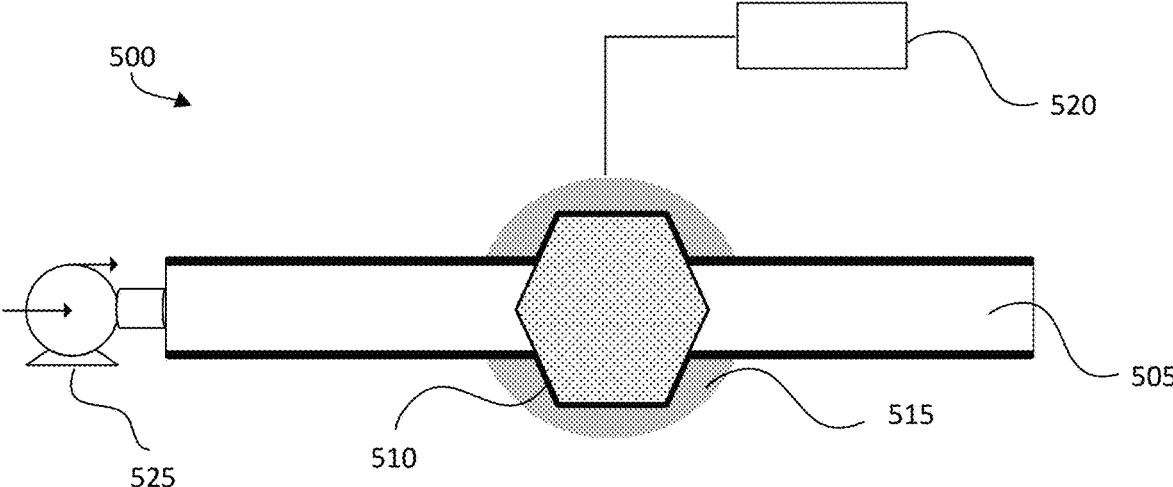
FIG. 5 is a schematic diagram of a system for extracting nucleic acids according to embodiments of the present invention.

FIG. 5 is a schematic diagram of a system for extracting nucleic acids according to embodiments of the present invention. The system 500 is configured to extract nucleic acids from a biological sample. The system 500 includes a fluid conduit 505. The fluid conduit 505 includes a chamber 510 for receiving one or more fluids. The chamber 510 is disposed at a location along a length of the fluid conduit 505. The chamber may have a cross-sectional area larger than an average cross-sectional area of the fluid conduit. The fluid conduit 505 includes a magnetic field source 515 that is coupled to a controller 520. A controller 520 can be coupled to the magnetic field source 515. In some embodiments, the fluid conduit 505 includes a plurality of magnetic field sources along discrete regions of the chamber 510 that are each controlled by the controller 520. The controller 520 is configured to move (e.g., oscillate) the magnetic field source (e.g., turn the magnetic field on or off). For example, the controller 520 can be configured to vary (e.g., oscillate) the magnetic field source 515 in any direction within the chamber 510 between two different magnetic field sources. In some embodiments, the system 500 includes a pump 525 configured to pump a plurality of fluids through the fluid conduit 505.

Figure 6E:
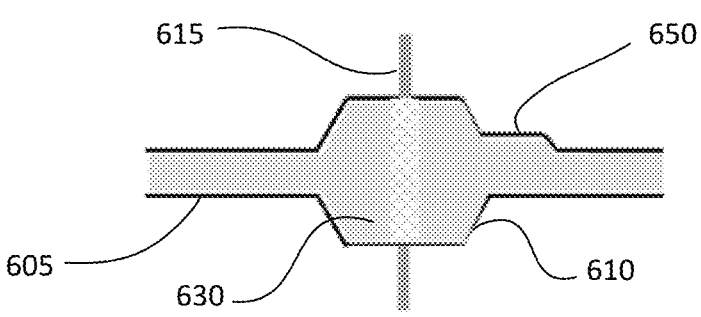

FIGS. 6A-H are simplified schematic cross-sectional view diagrams illustrating a fluid conduit extraction system according to another embodiment of the present invention. As shown in FIG. 6A, the system for extracting nucleic acids 600 comprises a fluid conduit 605. The fluid conduit 605 includes a chamber 610 for retaining a solid-phase substrate within a predetermined region of the fluid conduit. One or more magnets 615 are disposed around or within the chamber 610. In some embodiments, the one or more magnets 615 apply a magnetic field to an area of the chamber that is smaller than at least one dimension of the chamber. For example, the magnetic field produced by the one or more magnets 615 may be smaller than the length of the chamber 610 to trap a solid-phase substrate within the chamber 610. In some embodiments, the length, height, and width of the magnetic field applied by the one or more magnets 615 can be smaller than, larger than, or about the same size as the chamber 610. FIG. 6A shows a slug of sample fluid 620 as it begins to flow through the fluid conduit 605 from left to right. In some embodiments, the sample fluid 620 flows through the fluid conduit 605 from right to left. In some embodiments, the slug of sample fluid 620 comprises target biological molecules bound to a solid-phase substrate.

In some embodiments, the fluid conduit 605 may include a fluid trapping region 650. The fluid trapping region 650 can be adjacent or within the chamber 610. For example, the fluid trapping region 650 can be a region that tapers from the chamber 610 to the fluid conduit 605. In some embodiments, the fluid trapping region 650 is a cavity within the chamber 610. The fluid trapping region 650 is configured to trap or hold an immiscible fluid. The fluid trapping region 650 can be used to trap any immiscible fluid so that it does not block the flow of the elution buffer over the solid-phase substrate as further discussed herein.

FIG. 6B shows the solid-phase substrate in the sample fluid 620 trapped within chamber 610, which can also be referred to as a trapping site. The one or more magnets 615 can be selectively controlled to change or move the magnetic field from the magnets 615 to different locations with respect to the chamber 610. When the slug of sample fluid 620 passes through the fluid conduit 605, the magnets 615 can apply a magnetic field to trap the solid-phase substrate in the slug of sample fluid 620 at the trapping site. In this way, the solid-phase substrate in the sample fluid 620 is trapped in the chamber 610.

FIG. 6C shows the supernatant 625 separated from the sample fluid 620. The target biological molecules bound to the solid-phase substrate in the sample fluid 620 are trapped in the chamber 610 of the fluid conduit 605 using a magnetic field source 615, which can be supplemented by physical structures as illustrated in FIG. 4. The supernatant 625 (e.g., the unbound portion of the sample fluid) continues through the fluid conduit 605. FIG. 6D shows a slug of immiscible fluid 630 introduced into the fluid conduit 605. In some embodiments, the immiscible fluid directly displaces the sample fluid or other wash buffers. In other embodiments, there is an air gap between the two fluids. In some embodiments, the slug of immiscible fluid 630 moves through the fluid conduit 605 from left to right or vice versa.

FIG. 6E shows the slug of immiscible fluid 630 filling the chamber 610. In some embodiments, the slug of immiscible fluid 630 flows through the fluid conduit after one or more wash buffers flow through the fluid conduit 605. In some embodiments, one or more slugs of immiscible fluid 630 flow through the fluid conduit, alternating with the one or more slugs of wash buffer, with the last slug being an immiscible fluid to remove any residual wash buffer. The slug of immiscible fluid 630 flows through the fluid conduit 605 and passes over and through the solid-phase substrate trapped by the magnetic field in the chamber 610 of the fluid conduit 605. In some embodiments, after a wash buffer (e.g., ethanol slug) has passed through the fluid conduit 605, the slug of immiscible fluid 630 is introduced into the fluid conduit 605. The slug of immiscible fluid 630 removes trace elements of wash buffer from the fluid conduit and/or the surface of the solid-phase substrate.

Figure 6F:
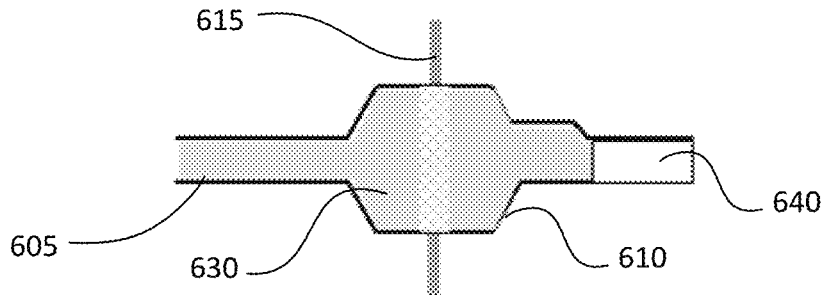

FIG. 6F shows a slug of elution buffer 640 introduced into the fluid conduit 605 to displace the immiscible fluid and release the target biological molecules from the solid phase substrate into the elution buffer. In this embodiment, the slug of elution buffer 640 can flow through the fluid conduit 605 from right to left. In some embodiments the slug of elution buffer 640 is introduced in the opposite direction from the direction of flow of the immiscible fluid 630. In other embodiments, the elution buffer and immiscible fluid are introduced in the same direction. The elution buffer is kept in contact with the solid phase substrate in the chamber 610 to allow for target molecule elution.

Figure 6G:
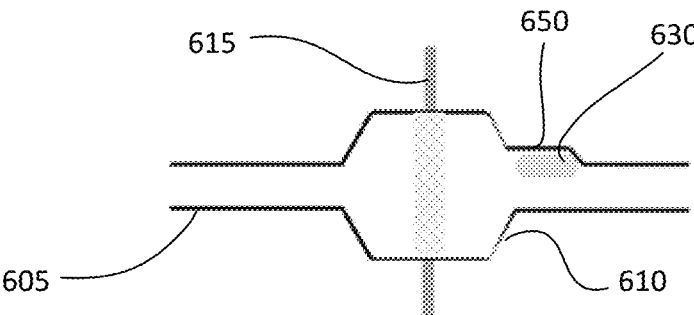

FIG. 6G shows the fluid trapping region 650 trapping the immiscible fluid 630 adjacent or within the chamber 610.

The fluid trapping region 650 can be used to trap any stray immiscible fluid 630 so that it does not block the flow of the elution buffer over the solid-phase substrate. The fluid trapping region 650 can be disposed on the proximal side of the trapped solid-phase substrate with respect to the flow of the elution buffer. In some embodiments, the fluid trapping region 650 comprises a region of the chamber 610 or fluid conduit 605 having a larger cross sectional area than the rest of the chamber 610 or fluid conduit 605. In some embodiments, the fluid trapping region 650 is located in a top region of the chamber 610 or fluid conduit 605 so that gravity will act to force the lower density immiscible fluid into the fluid trapping region 650. In some embodiments, the fluid trapping region 650 is surface treated to preferentially hold the immiscible fluid compared to the elution buffer (e.g. using an oleophilic coating within a hydrophilic chamber/conduit when using an oil-based immiscible fluid).

Figure 6H:
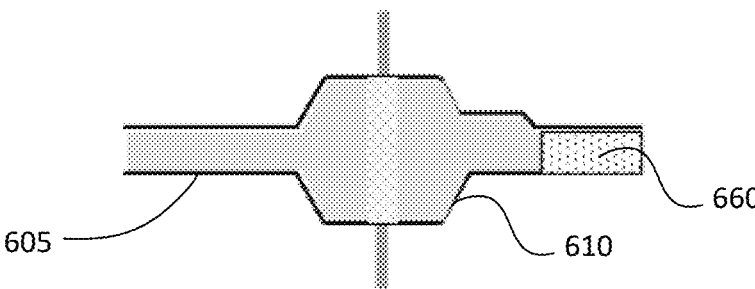

FIG. 6H shows the re-introduction of an immiscible fluid (from the left to the right) to push the elution buffer containing the eluate 660 into the conduit for transport to other parts of the system. In some embodiments, there is an air gap between the two fluids. In some embodiments, air is used to push the elution buffer out of the chamber and into the conduit.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. A method for extracting nucleic acids, the method comprising:

mixing a biological sample with a lysis buffer and solid-phase substrate to produce a sample fluid, wherein nucleic acids in the sample fluid bind to the solid-phase substrate;

flowing the sample fluid comprising the nucleic acids bound to the solid-phase substrate in a fluid conduit to a trapping site, wherein the trapping site comprises a chamber;

applying a magnetic field to trap the solid-phase substrate of the sample fluid flowing through the fluid conduit at the trapping site to retain the solid-phase substrate in the chamber;

flowing an immiscible fluid through the fluid conduit through the trapping site including the retained solid-phase substrate to remove residual sample fluid, wherein the immiscible fluid comprises one or more of mineral oil, silicone oil, hexadecane, paraffin oil, fluorinerts, fluorinated oils, or mixtures thereof; and flowing an elution buffer through the fluid conduit to elute nucleic acids from the solid-phase substrate after flowing the immiscible fluid, wherein flowing the elution buffer through the fluid conduit comprises flowing the elution buffer in a direction opposite to a direction of flow of the immiscible fluid;

wherein the method does not include flowing air through the fluid conduit to dry either the fluid conduit or the solid-phase substrate.

2. The method of claim 1, further comprising flowing a wash buffer through the fluid conduit to remove impurities from the solid-phase substrate, wherein flowing the immiscible fluid occurs after flowing the wash buffer.

3. The method of claim 2, wherein the wash buffer comprises an alcohol-based wash buffer comprising ethanol or propanol.

4. The method of claim 2, further comprising applying a time varying magnetic field to move the solid-phase substrate in the fluid conduit, wherein the magnetic field is configured to maintain sufficient force on the solid-phase substrate to keep the solid-phase substrate trapped during at least one of:

flowing the wash buffer through the fluid conduit;

flowing the immiscible fluid through the fluid conduit; or flowing the elution buffer through the fluid conduit.

5. The method of claim 1, wherein the chamber has a cross-sectional area at least 10% larger than an average cross-sectional area of the fluid conduit, wherein the chamber is characterized by a hexagonal shape.

6. The method of claim 2, further comprising varying the magnetic field to move the solid-phase substrate in the chamber during at least one of:

flowing the wash buffer through the fluid conduit;

flowing the immiscible fluid through the fluid conduit; or flowing the elution buffer through the fluid conduit.

7. The method of claim 1, wherein the eluted nucleic acids from the solid-phase substrate are transferred into the elution buffer, wherein flowing the elution buffer comprises flowing the eluted nucleic acids away from the trapping site.

8. The method of claim 1, wherein the solid-phase substrate comprises a plurality of beads, paramagnetic beads, magnetic beads, glass beads, glass, or glass fibers.

9. The method of claim 8, wherein the solid-phase substrate comprises a coating comprising silica, ceramic, polymers, oligonucleotides, or mixtures thereof.

10. The method of claim 1, wherein the fluid conduit comprises a fluid trapping region configured to receive the immiscible fluid.

11. The method of claim 1, wherein the magnetic field is applied to an area of the chamber that is smaller than at least one dimension of the chamber.

\* \* \* \* \*